US00PP11243P

United States Patent [19]

Bloom

[11] Patent Number: Plant 11,243

[45] Date of Patent: Feb. 29, 2000

[54] HELENIUM PLANT NAMED 'COPPELIA'

[75] Inventor: Alan H. V. Bloom, Norfolk, United Kingdom

[73] Assignee: Blooms of Bressingham Ltd., Norfolk, United Kingdom

[21] Appl. No.: 08/878,941

[22] Filed: Jun. 19, 1997

[51] Int. Cl.[7] ..... A01H 5/00

[52] U.S. Cl. ..... Plt./263

[58] Field of Search ..... Plt./68.1, 263

[56] References Cited

PUBLICATIONS

Anthony Huxley; The New Royal Horticultural Society Dictionary of Gardening; p. 520; 1992.

*Primary Examiner*—Douglas W. Robinson
*Assistant Examiner*—Kent L. Bell
*Attorney, Agent, or Firm*—Foley & Lardner

[57] ABSTRACT

A new and distinct cultivar of Helenium plant named 'Coppelia', characterized by its single daisy-like coppery orange ray florets, with each floret being tipped orange yellow, and its flowering which commences late July and continues to early October. 'Coppelia' forms compact groups of erect leafy stems which are ideal for use in borders.

2 Drawing Sheets

The present invention relates to a new and distinct cultivar of hardy perennial herbaceous plant of the genus Helenium, a member of the Compositae family, with the new cultivar being known by its cultivar name 'Coppelia'.

This new cultivar of Helenium arose as a seedling form a breeding program carried out by the inventor Alan H. V. Bloom in Norfolk, England. The female parent was a presently unidentified cultivar of the species *Helenium autumnale*, and the male parent was a presently unidentified cultivar of the species *Helenium bigelovi*.

The original selection of the new cultivar was reproduced asexually by the inventor in Norfolk, England by vegetative propagation using basal cuttings. Each of the progeny of the first and second generations has been found to retain the characteristics of the original selection.

'Coppelia' has achieved the aim of being a quality flowering perennial with a shorter flowering height and flowers that do not reflex completely. The small, almost insignificant linear-lanceolate basal leaved clumps offer support to the erect leafy stems carrying the flowers. The classic single daisy-like flowers make an excellent display of coppery orange ray florets issuing from a central conical disc.

The new cultivar blooms from late July to early October in Norfolk, England. The flowers resemble those of typical *H. autumnale* cultivars in habit but not in color. 'Coppelia' also has a resemblance to Helenium 'Bruno' (unpatented) and Helenium 'Butterpat' (unpatented) both in habit and in flower shape.

The plant thrives best in full sun and well drained soil.

The accompanying photographic drawings show typical flower and foliage characteristics of 'Coppelia', with colors being as true as possible with illustrations of this type. In this regard, the illustration may not depict the color designations and descriptions as they accurately appear in the botanical description.

DESCRIPTION OF THE PHOTOGRAPHIC DRAWINGS

DETAILED DESCRIPTION

Figure 1:
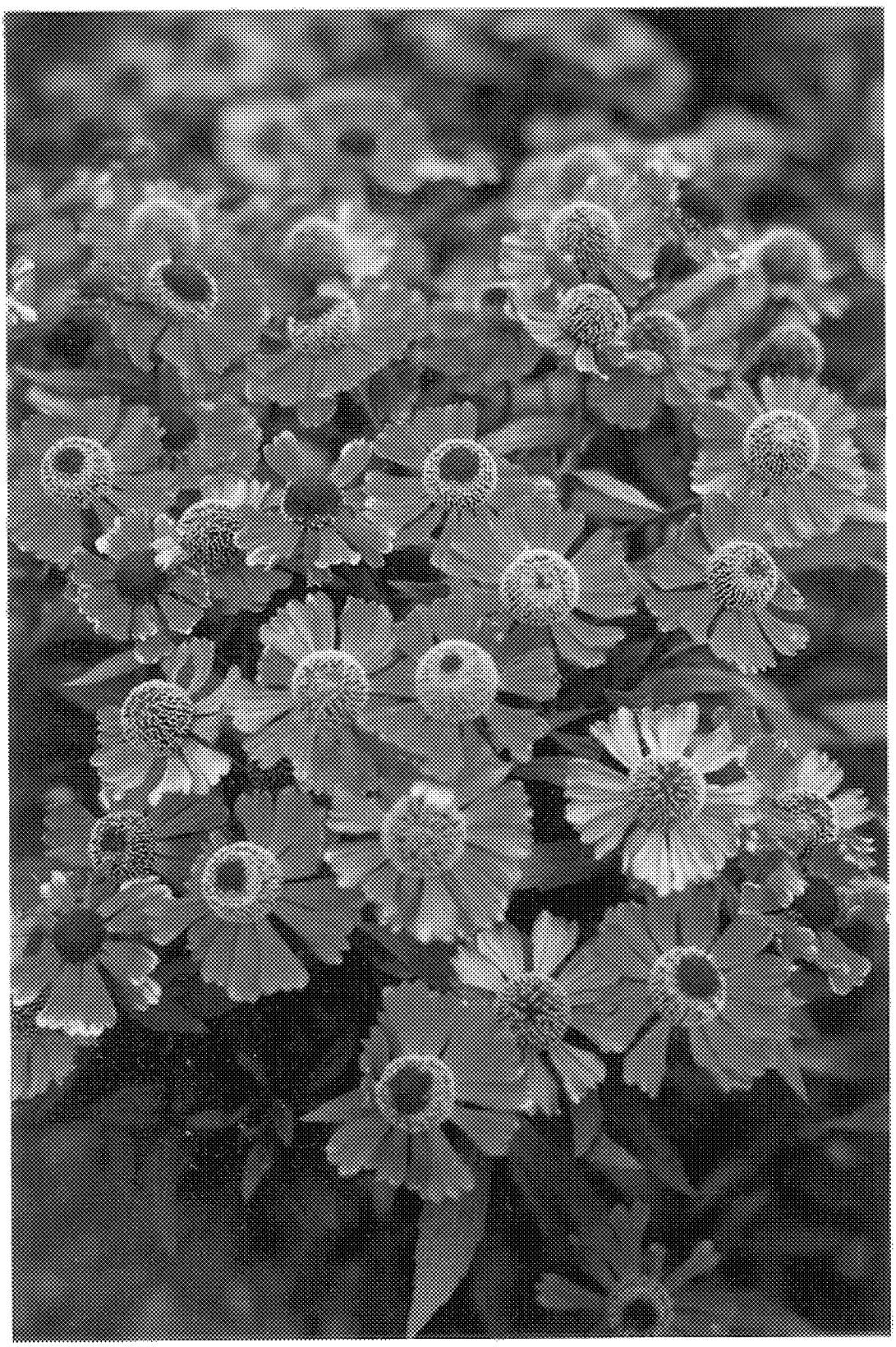
FIG. 1 is a close up view of the flowers.
Figure 2:
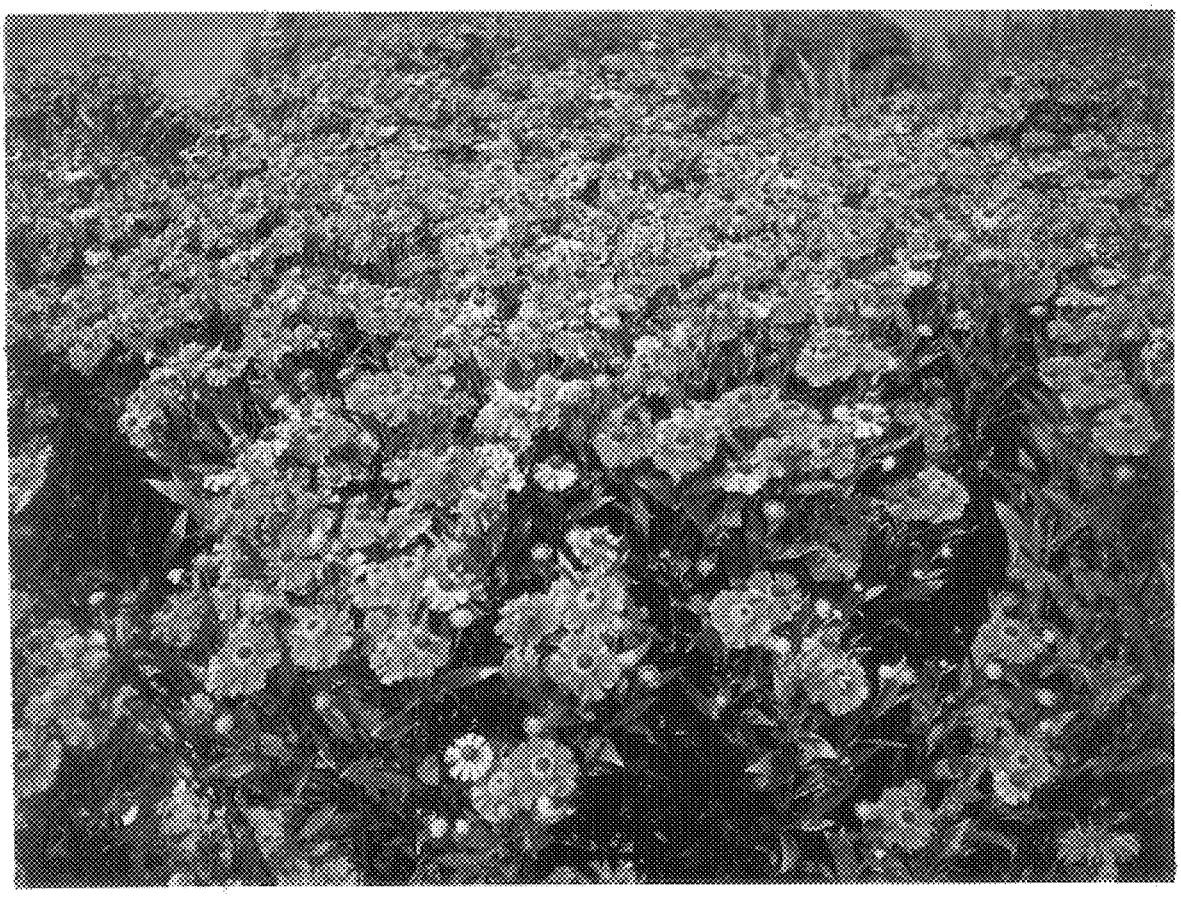
FIG. 2 is a view of the plant growing in a border setting.

The following is a detailed description of the new cultivar. All color determinations and comparisons are based on The Royal Horticultural Society Colour Chart.

Origin: Seedling selection.
Parentage: *Helenium autumnale*×*Helenium bigelovi*.
Plant:

- *Habit.*—Basal leaves with erect leafy flowering stems.
- *Size.*—Mature plants are 100 cm in height with a spread of 45 cm.
- *Root system.*—Fibrous.
- *Plant vigor.*—A perennial that shows vigorous and healthy growth throughout Great Britain.
- *Blooming habits.*—From late July continuing into early October.
- *Lastingness of bloom.*—10–20 Days.
- *Hardiness.*—Winter hardy throughout the British Isles. The plant has not been fully tested for maximum summer tolerance above 32° C. (90° F.).

Foliage:

- *Arrangement.*—Linear to lanceolate serrated leaves.
- *Type.*—Herbaceous perennial.
- *Texture.*—Both upper and lower surfaces smooth and dull.
- *Length.*—10 cm to 15 cm.
- *Width.*—1 cm to 3 cm.
- *Margins.*—Serrate.
- *Apex.*—Acute.
- *Base.*—Cuneate.
- *Stems.*—Leafy, erect, ribbed, and decurrent, extending between leaf joints, becoming corymbosely branched as inflorescences set; pithy, but not hollow, containing latex or oil canals; mature stems are stiff and not easily broken, immature stems bend easily without breaking; length is about 100 cm; color of immature stems is R.H.S. 139A, mature stems are R.H.S. 139C. with speckles of R.H.S. 184C.
- *Peduncle.*—Pithy, but not hollow, containing latex or oil canals; individual branched peduncles are 8–45 cm; color of immature peduncles is R.H.S. 139A, mature peduncles are R.H.S. 139C with speckles of R.H.S. 184C.

Inflorescence: Clustered as a corymb; each individual inflorescence is about 12 cm in diameter;

*Disc florets.*—Arranged as a central conical disc.

*Disc florets size.*—1.5 to 2 cm in length.

*Disc floret, aspect.*—Rounded.

*Disc floret, texture.*—Smooth and soft to the touch.

*Disc floret, quantity.*—Numerous.

*Ray florets.*—15 individual ray florets of similar size.

*Ray floret, size.*—3 cm 4 cm in length and 0.5 cm to 1 cm in width.

*Ray floret, shape.*—Obovate.

*Ray floret, texture.*—Smooth and soft to the touch.

*Ray floret, margin.*—Entire.

*Ray, floret, tip.*—Tri-lobed.

*Inflorescence shape.*—Circular.

*Inflorescence type.*—Corymb, containing up to 24 blooms with each bloom lasting 10–20 days during different stages of the flowering season; each single inflorescence is supported by a single peduncle.

*Carpels.*—1 celled.

*Fragrance.*—A slight or very weak fragrance has been observed.

Reproductive organs:

*Androecium.*—Stamens: 5, united to form a cylinder around the style; color is greyed-red 182A, which changes to yellow-orange R.H.S. 21B, as inflorescences mature. Filaments: United to form a cylinder; color is greyed-red 182A, which changes to yellow-orange R.H.S. 21B, as inflorescences mature. Anthers: Sagittate; color is greyed-red 182A, which changes to yellow-orange R.H.S. 21B, as inflorescences mature. Pollen: Scant; color is R.H.S. 17B.

*Gynoecium.*—Pistils: There is one pistil in each of the cylinders formed by the stamens. The color is yellow-orange, R.H.S. 21A. Ovary: Inferior and single-celled. The color is yellow-green, R.H.S. 154A. Androecium and Gynoecium are present on both ray and disc florets.

Color characteristics:

*Foliage.*—Mature leaves: upper surface R.H.S. 137A, under surface R.H.S. 137B.

*Inflorescence.*—Top surface ray floret color is R.H.S. 182A, with the end of each ray floret being R.H.S. 21A; under surface ray floret color R.H.S. 182B; the color of the tips of the ray florets is R.H.S. 21B, which increases towards the base of the florets (upper and under surfaces) as the inflorescences mature. The color of the disc florets is R.H.S. 182A, which changes to R.H.S. 21B as the inflorescences mature.

Other characteristics: A small amount of seed is set, which has not be found to be viable; seed color is dull grey/brown, R.H.S. 199B.

I claim:

1. A new and distinct cultivar of Helenium plant named 'Coppelia' as shown and described.

* * * * *